US011712551B2

(12) United States Patent
Bae

(10) Patent No.: US 11,712,551 B2
(45) Date of Patent: Aug. 1, 2023

(54) ATTACHING/DETACHING DEVICE AND MULTI-DOSE INJECTION APPARATUS

(71) Applicant: NEMOTO KYORINDO CO., LTD., Tokyo (JP)

(72) Inventor: Kyongtae T. Bae, Tokyo (JP)

(73) Assignee: NEMOTO KYORINDO CO., LTD., Tokyo (JP)

( * ) Notice: Subject to any disclaimer, the term of this patent is extended or adjusted under 35 U.S.C. 154(b) by 648 days.

(21) Appl. No.: 16/634,108

(22) PCT Filed: Jul. 24, 2018

(86) PCT No.: PCT/JP2018/027700
§ 371 (c)(1),
(2) Date: Jan. 24, 2020

(87) PCT Pub. No.: WO2019/022073
PCT Pub. Date: Jan. 31, 2019

(65) Prior Publication Data
US 2020/0206490 A1     Jul. 2, 2020

(30) Foreign Application Priority Data

Jul. 27, 2017   (JP) .................................. 2017-145844

(51) Int. Cl.
*A61M 39/10* (2006.01)
*A61M 39/20* (2006.01)
(Continued)

(52) U.S. Cl.
CPC .......... *A61M 39/105* (2013.01); *A61M 5/007* (2013.01); *A61M 5/1408* (2013.01);
(Continued)

(58) Field of Classification Search
CPC .... A61M 39/105; A61M 39/20; A61M 39/14; A61M 5/1408; A61M 5/007;
(Continued)

(56) References Cited

U.S. PATENT DOCUMENTS

| 8,231,584 B2 | 7/2012 | Peters |
| 2007/0073215 A1* | 3/2007 | Wieslander ........... A61M 39/18 604/29 |

(Continued)

FOREIGN PATENT DOCUMENTS

| EP | 0 925 797 A1 | 6/1999 |
| JP | H04-354953 A | 12/1992 |

(Continued)

OTHER PUBLICATIONS

The extended European search report issued by the European Patent Office dated Nov. 27, 2020, which corresponds to European Application No. 18838007.5-1122 and is related to U.S. Appl. No. 16/634,108.

(Continued)

*Primary Examiner* — Lauren P Farrar
*Assistant Examiner* — Hamza A Darb
(74) *Attorney, Agent, or Firm* — Studebaker & Brackett PC

(57) ABSTRACT

A first tube connector and a second tube connector are to be automatically and mechanically attached to and detached from each other. Provided is an attaching/detaching device (100) including: a fixing portion (104) configured to fix a first tube connector (105); a holding portion (107) configured to hold a second tube connector (106); a moving portion configured to move the holding portion (107), which holds the second tube connector (106), in a direction of approaching the first tube connector (105) to connect the second tube connector (106) to the first tube connector (Continued)

(105), and move the second tube connector (106) after the connection in a direction of separating from the first tube connector (105) to release the connection of the second tube connector (106) and the first tube connector (105).

13 Claims, 10 Drawing Sheets

(51) Int. Cl.
| | |
|---|---|
| *A61M 39/18* | (2006.01) |
| *A61M 5/00* | (2006.01) |
| *A61M 5/14* | (2006.01) |
| *A61M 5/162* | (2006.01) |
| *A61M 5/142* | (2006.01) |
| *A61M 5/168* | (2006.01) |

(52) U.S. Cl.
CPC .......... *A61M 5/1411* (2013.01); *A61M 5/162* (2013.01); *A61M 5/16827* (2013.01); *A61M 39/20* (2013.01); *A61M 2005/1402* (2013.01)

(58) Field of Classification Search
CPC .............. A61M 5/162; A61M 39/1411; A61M 5/1687; A61M 5/1411; A61M 5/16827; A61M 2005/1402; A61M 2039/1016; A61M 5/1422; A61M 5/16886; A61M 39/1011; A61M 39/18; A61M 39/10; A61M 2039/1033; A61M 39/1055
See application file for complete search history.

(56) References Cited

U.S. PATENT DOCUMENTS

| | | |
|---|---|---|
| 2008/0086094 A1 | 4/2008 | Peters |
| 2009/0012448 A1* | 1/2009 | Childers ................ A61M 1/14 |
| | | 604/29 |
| 2010/0130920 A1 | 5/2010 | Lo et al. |

FOREIGN PATENT DOCUMENTS

| | | |
|---|---|---|
| JP | H08-725 A | 1/1996 |
| JP | 2008-541813 A | 11/2008 |
| WO | 85/00979 A1 | 3/1985 |
| WO | 99/02205 A1 | 1/1999 |

OTHER PUBLICATIONS

International Preliminary Report on Patentability issued in PCT/JP2018/027700; dated Jan. 28, 2020.
International Search Report issued in PCT/JP2018/027700; dated Sep. 25, 2018.

* cited by examiner

ATTACHING/DETACHING DEVICE AND MULTI-DOSE INJECTION APPARATUS

TECHNICAL FIELD

The present invention relates to an attaching/detaching device and a multi-dose injection apparatus including the attaching/detaching device.

BACKGROUND ART

In Patent Literature 1, there is disclosed a fluid delivery system which connects a dispensing unit and a dosing device (injection needle) configured to dispense a fluid to a subject. This fluid delivery system includes a first tubing and a second tubing. The first tubing is connected to the second tubing and the dispensing unit. The second tubing is connected to the dosing device and the first tubing. Moreover, the first tubing includes a one-way valve. The one-way valve which permits a fluid flow from the dispensing unit toward the dosing device but prevents a fluid backward flow from the dosing device toward the dispensing unit. The first tubing and the second tubing are in a fluid connection with each other by means of a connection device which is attachable to and detachable from each other.

CITATION LIST

Patent Literature

PTL 1: Japanese Patent Application Laid-Open No. 2008-541813

SUMMARY OF INVENTION

Technical Problem

A part of the fluid delivery system disclosed in Patent Literature 1 is reusable. For such a configuration, the connection device of the fluid delivery system includes a first connector part and a second connector part which are attachable to and detachable from each other. The first connector part includes, for example, a luer lock flange which is adapted to be received in a duct of the second connector part. Further, the first connector part and the second connector part can be manually attached to and detached from each other.

With the fluid delivery system, a connection work for a flow passage to be reused, which is provided on the injection apparatus side, and a flow passage to be discarded, which is provided on the subject side, is complicated. Further, when a blood backflow occurs immediately after injection of a chemical liquid, there is a risk in that the reused portion is contaminated due to passage of the blood through the one-way valve.

Solution to Problem

In order to solve the above-mentioned problem, an attaching/detaching device according to one aspect of the present invention includes: a fixing portion configured to fix a first tube connector; a holding portion configured to hold a second tube connector; a moving portion configured to move the holding portion, which holds the second tube connector, in a direction of approaching the first tube connector to connect the second tube connector to the first tube connector, and move the second tube connector after the connection in a direction of separating from the first tube connector to release the connection of the second tube connector and the first tube connector.

Advantageous Effects of Invention

With this configuration, the first tube connector and the second tube connector are automatically and mechanically attachable to and detachable from each other. Thus, the connection work for the flow passages can easily be performed. Moreover, the first tube connector and the second tube connector are physically separated from each other immediately after injection of a chemical liquid. Therefore, even when the blood backflow occurs, contamination on an upstream side of the attaching/detaching device (injection apparatus side) can be prevented.

Further features of the present invention will become apparent from the following description of exemplary embodiments referring to the attached drawings.

DESCRIPTION OF EMBODIMENTS

Now, illustrative embodiments for carrying out the present invention are described in detail with reference to the drawings. However, for example, dimensions, materials, shapes, and relative positions of components described in the following embodiments may be freely selected and can be changed depending on a configuration of an apparatus to which the present invention is applied or on various conditions. Moreover, unless otherwise particularly described, the scope of the present invention is not limited to the embodiments which are specifically described below. In the description of the injection apparatus in Description, a side on which a syringe is mounted corresponds to a front side, and a side opposite thereto corresponds to a rear side.

First Embodiment

Figure 1:
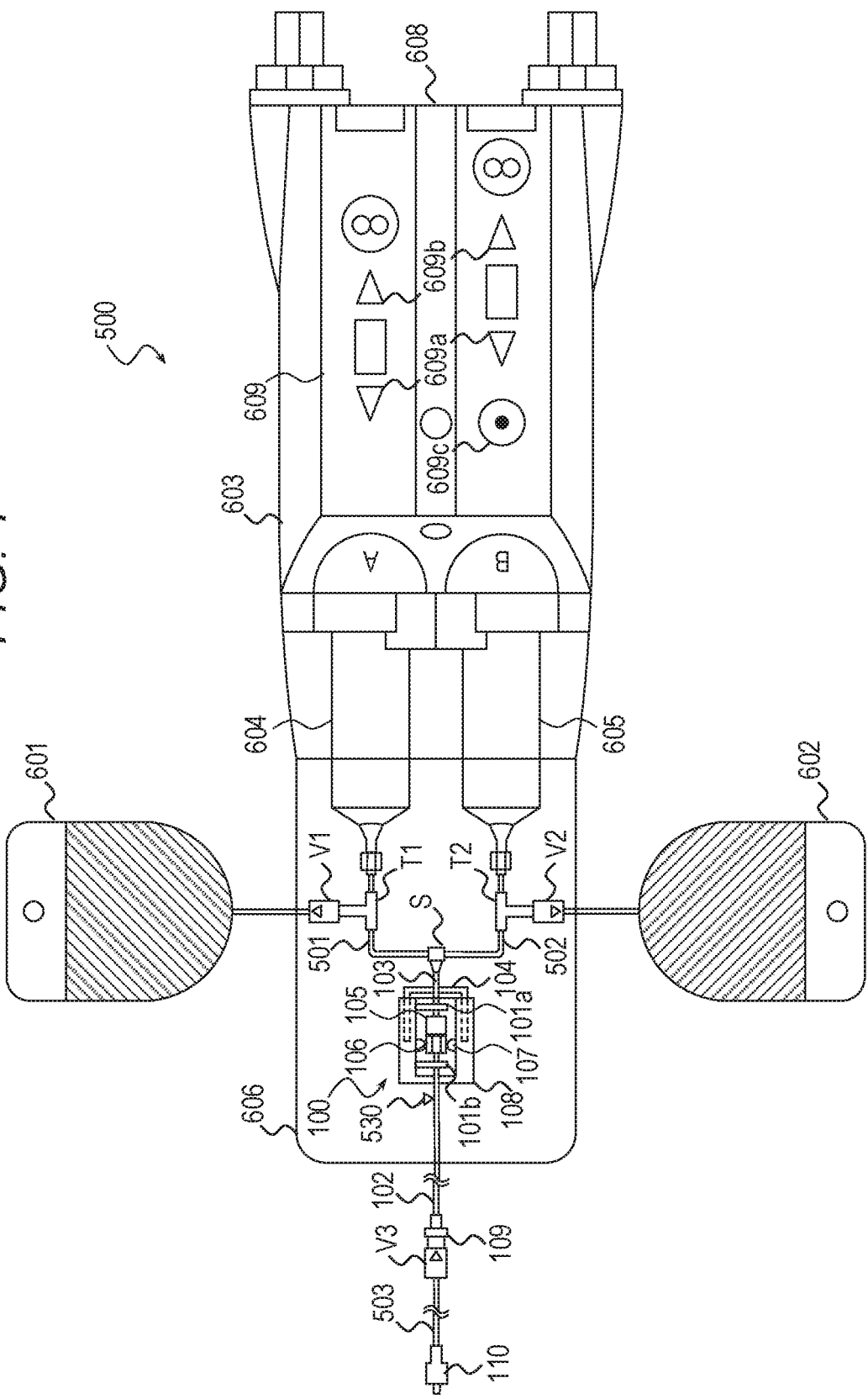
FIG. 1 is a schematic view for illustrating a chemical liquid circuit.

FIG. 1 is a schematic view for illustrating an injection system 500 which is capable of performing multi-dose injection of a chemical liquid, and is an illustration of a state in which flow passages are connected. The injection system 500 includes a multi-dose injection apparatus 608 which is capable of performing multi-dose injection of a chemical liquid. Moreover, the injection system 500 is to be used at the time of sucking a first chemical liquid for medical use such as a contrast medium and a second chemical liquid for medical use such as a physiological saline solution from respective chemical liquid supply sources into syringes and injecting the chemical liquids to a subject being an imaging subject. A contrast-medium chamber 601 serving as a first-chemical-liquid supply source and a physiological-saline-solution chamber 602 serving as a second-chemical-liquid supply source are connected to the injection system 500.

Moreover, the injection system 500 includes a contrast-medium line 501 and a physiological-saline-solution line 502. The contrast-medium line 501 and the physiological-saline-solution line 502 each include, for example, a suction tube serving as a tube for allowing a chemical liquid to flow therethrough. Herein, the line corresponds to a flow passage for allowing a liquid to flow therethrough and includes various members (for example, various tubes, a T-shaped connector, a male connector, a female connector, a one-way valve, a connection pipe, a mixing device, a stop cock, and a rotator).

The contrast-medium line 501 includes tubes, a first T-shaped connector T1, and a first one-way valve V1. The contrast-medium chamber 601 is connected to a mixing device S (for example, "SPIRAL FLOW" (trademark) manufactured by Nemoto Kyorindo Co., Ltd.) and to a distal end of a contrast-medium syringe 604 or a tube connected to the contrast-medium syringe 604, through intermediation of the tubes, the first one-way valve V1, and the first T-shaped connector T1.

Similarly, the physiological-saline-solution line 502 includes tubes, a second T-shaped connector T2, and a second one-way valve V2. The physiological-saline-solution chamber 602 is connected to a mixing device S and to a distal end of a physiological-saline-solution syringe 605 or a tube connected to the physiological-saline-solution syringe 605, through intermediation of the tubes, the second one-way valve V2, and the second T-shaped connector T2. That is, the contrast-medium line 501 and the physiological-saline-solution line 502 are in a fluid connection with each other through intermediation of the mixing device S. Alternatively, the contrast-medium line 501 and the physiological-saline-solution line 502 may be connected to each other through intermediation of a T-shaped connector.

Moreover, the contrast-medium line 501 is connected to the contrast-medium chamber 601 through intermediation of a spike needle having a drip chamber (not shown). The contrast-medium chamber 601 is, for example, a bottle-like container charged with the contrast medium, and is used while being hung by a hanger (not shown) (for example, a hanger mounted to the multi-dose injection apparatus 608). The contrast medium having flowed out from the contrast-medium chamber 601 drops as droplets into the drip chamber of the spike needle having a drip chamber and flows to the contrast-medium line 501.

Similarly, the physiological-saline-solution line 502 is connected to the physiological-saline-solution chamber 602 through intermediation of a spike needle having a drip chamber (not shown). The physiological-saline-solution chamber 602 is, for example, a bottle-like container charged with the physiological saline solution, and is used while being hung by a hanger (not shown). The physiological saline solution having flowed out from the physiological-saline-solution chamber 602 drops as droplets into the drip chamber of the spike needle having a drip chamber and flows to the physiological-saline-solution line 502.

In the injection system 500, the first one-way valve V1, the second one-way valve V2, and a third one-way valve V3 are each a pressure-resistant one-way valve configured to permit a flow in a downstream direction and blocks a flow in an upstream direction. In FIG. 1, a triangle mark added to each one-way valve indicates a direction of blocking the chemical liquid, and a distal end of the triangle indicates a direction in which the chemical liquid does not flow. For example, the triangle added to the first one-way valve V1 connected to the contrast-medium line 501 indicates that the contrast medium does not flow toward the contrast-medium chamber 601 (upstream direction).

Specifically, the first one-way valve V1 is mounted to the first T-shaped connector T1. The first one-way valve V1 permits a flow in a direction toward a first tube 103 and blocks a flow in a direction toward the contrast-medium chamber 601. Moreover, the second one-way valve V2 is mounted to the second T-shaped connector T2. The second one-way valve V2 permits a flow in a direction toward the first tube 103 and blocks a flow in a direction toward the physiological-saline-solution chamber 602. Moreover, the third one-way valve V3 is mounted to a tube of a subject line 503. The third one-way valve V3 permits a flow in a direction toward a subject and blocks a flow in a direction toward the multi-dose injection apparatus 608.

With those one-way valves, when the contrast medium is sucked toward the contrast-medium syringe 604, the contrast medium flows from the contrast-medium line 501 toward the contrast-medium syringe 604. When the contrast medium is discharged toward the subject line 503, the contrast medium does not flow back toward the contrast-medium chamber 601. Moreover, when the physiological saline solution is sucked toward the physiological-saline-solution syringe 605, the physiological saline solution flows from the physiological-saline-solution line 502 toward the physiological-saline-solution syringe 605. When the physiological saline solution is discharged toward the subject line 503, the physiological saline solution does not flow back toward the physiological-saline-solution chamber 602.

The multi-dose injection apparatus 608 sucks the chemical liquids from the contrast-medium chamber 601 and the physiological-saline-solution chamber 602 and injects the chemical liquids into a subject. The contrast-medium syringe 604 being a first syringe and the physiological-saline-solution syringe 605 being a second syringe are mounted to the multi-dose injection apparatus 608. The contrast-medium syringe 604 and the physiological-saline-solution syringe 605 are fixed to a syringe protection case under a state in which plungers (not shown) are mounted to the syringes. The syringe protection case is fixed to the multi-dose injection apparatus 608 by a syringe clamper.

The multi-dose injection apparatus 608 includes pressers (not shown) which are engaged with the plungers of the syringes, respectively. The multi-dose injection apparatus 608 moves each plunger in a forward direction (advance) or in a backward direction (retreat). Moreover, the multi-dose injection apparatus 608 includes an operation portion 609. The operation portion 609 includes advance buttons 609a, retreat buttons 609b, and a stop button 609c. Moreover, the operation portion 609 may include operation buttons such as a start button and a priming button. Further, remote operation devices (not shown) such as a foot switch and a hand switch are connected to the multi-dose injection apparatus 608 in a wire connection or in a wireless connection.

Moreover, the multi-dose injection apparatus 608 is turnably connected to a caster stand placed on a floor surface. With such a configuration, the multi-dose injection apparatus 608 can be turned between a posture in which the front side of the multi-dose injection apparatus 608 is oriented toward the floor surface and a posture in which the rear side of the multi-dose injection apparatus 608 is oriented toward the floor surface. It is preferred that the multi-dose injection apparatus 608 be connected to the caster stand so as to be capable of turning in a right-and-left direction. Alternatively, the multi-dose injection apparatus 608 can be connected to a hanging member so as to be hung from a ceiling, or can be connected to a catheter table or a catheter rail.

Further, the multi-dose injection apparatus 608 is connected to a control device (not shown) in a wire connection or in a wireless connection. For example, the multi-dose injection apparatus 608 is connected to the control device through a head cable. This control device includes a touch panel and functions as a controller for the multi-dose injection apparatus 608. Moreover, the control device stores, in advance, data of operation patterns (injection protocol) and data of chemical liquids. When a chemical liquid is to be injected into a subject, an operator operates the touch panel to input physical data of a subject and chemical liquid data to the control device. Examples of the physical data include an injection velocity, an injection amount, an injection time, and a weight. Examples of the chemical liquid data include an iodine amount and a kind of a chemical liquid.

The control device calculates an optimum injection condition based on input data and data stored in advance. Then, the control device determines an injection protocol including an injection amount of the chemical liquid for a subject based on the calculated injection condition. After that, in accordance with an operation by the operator, the multi-dose injection apparatus 608 injects the chemical liquid in accordance with the determined injection protocol. Alternatively, the control device can acquire the injection protocol and other data from an external storage medium.

The multi-dose injection apparatus 608 includes a base portion 606 extending from an injection head portion 603 to which the syringes are mounted. Further, an attaching/detaching device 100 described below, the contrast-medium line 501, and the physiological-saline-solution line 502 are at least partially received in a groove formed in the base portion 606. That is, the first one-way valve V1, the first T-shaped connector T1, the second one-way valve V2, the second T-shaped connector T2, the mixing device S, and the attaching/detaching device 100 (first tube 103 and second tube 102) are received in the groove. The groove has a shape complementary to corresponding members. Therefore, the members are arranged in the groove so as to be positioned with respect to the multi-dose injection apparatus 608.

[Attaching/Detaching Device]

The multi-dose injection apparatus 608 includes the attaching/detaching device 100 which is configured to be capable of connecting and separating the flow passage on the multi-dose injection apparatus 608 side and the flow passage on the subject side. The attaching/detaching device 100 includes a fixing portion 104 and holding portions 107. The fixing portion 104 is configured to fix a first tube connector 105. The holding portions 107 are configured to hold a second tube connector 106. Further, the attaching/detaching device 100 includes a moving portion 108. The moving portion 108 is capable of moving the holding portions 107, which hold the second tube connector 106, in a direction of approaching the first tube connector 105 and in a direction of separating from the first tube connector 105. The moving portion 108 moves the holding portions 107 in the direction of approaching the first tube connector 105 to connect the second tube connector 106 to the first tube connector 105. Moreover, the moving portion 108 moves the second tube connector 106, which has been connected, in the direction of separating from the first tube connector 105 to release the connection of the second tube connector 106 and the first tube connector 105.

The first tube connector 105 is, for example, a female luer connector provided at a distal end of the first tube 103 connected to the mixing device S. The first tube connector 105 is inserted into a slot (not shown) formed in the fixing portion 104 and fixed to the attaching/detaching device 100. Moreover, the second tube connector 106 is, for example, a male luer connector provided at a distal end of the second tube 102. The second tube connector 106 is nipped and held by a pair of fingers serving as the holding portions 107.

The second tube 102 is connected to the third one-way valve V3 through intermediation of a third tube connector 109. The third one-way valve V3 is mounted to the subject line 503 of the injection system 500. A catheter (not shown), which is to be inserted into a subject, is connected to the subject line 503. That is, the subject line 503 includes a fourth tube connector 110 to which the catheter is connected.

The moving portion 108 of the attaching/detaching device 100 is moved by a driving portion (not shown) so as to freely advance and retreat in the groove formed in the base portion 606. Specifically, the moving portion 108 and the fixing portion 104, which is fixed to the multi-dose injection apparatus 608, form a telescopic structure. Therefore, as the moving portion 108 moves relative to the fixing portion 104, an end portion of the fixing portion 104 is received in the moving portion 108. The driving portion is, for example, a DC motor, and is connected to a drive shaft of the moving portion 108 through intermediation of a gear train, a belt, or a pulley.

The pair of fingers serving as the holding portions 107 each have a substantially roller shape. The pair of fingers forwardly rotate or reversely rotate together with the movement of the moving portion 108. That is, the pair of fingers forwardly rotate while the moving portion 108 moves in a direction of approaching the fixing portion 104. Therefore, the second tube connector 106 is forwardly rotated by the pair of fingers to be brought into contact and threaded engagement with the first tube connector 105 in contact therewith. Meanwhile, the pair of fingers reversely rotate while the moving portion 108 moves in the direction of separating from the fixing portion 104. Therefore, the second tube connector 106 is reversely rotated by the pair of fingers to be disengaged and separated from the first tube connector 105.

With this configuration, a part of the injection system 500 located on the downstream side with respect to the first tube 103 can be used as a disposable part. Meanwhile, the first tube 103, the contrast-medium line 501, and the physiological-saline-solution line 502 can be reused. That is, after the second tube connector 106 is separated from the first tube connector 105, the subject line 503 and the second tube 102 can be discarded. The first tube 103, the contrast-medium line 501, and the physiological-saline-solution line 502 can be used again at the time of next injection of the chemical liquid.

For example, the holding portions 107 are each connected to the drive shaft of the moving portion 108 through intermediation of a gear train, a belt, or a pulley. With this configuration, the holding portions 107 forwardly rotate or reversely rotate in synchronization with the rotation of the drive shaft. Alternatively, in addition to the driving portion for the moving portion 108, there may be provided a driving portion for the holding portions 107. For example, the holding portions 107 may be driven with a motor other than the motor for the moving portion 108.

Further, the attaching/detaching device 100 includes latches as closing members configured to close the flow passages in the circuit. A drive source for the closing members is connected to an external controller in a wireless connection or in a wire connection and operates in accordance with a control signal from the controller to close the flow passages. For example, the multi-dose injection apparatus 608 functions as the controller.

Specifically, the attaching/detaching device 100 includes a first closing member 101a and a second closing member 101b. The first closing member 101a is configured to close the first tube 103 including the first tube connector 105. The second closing member 101b is configured to close the second tube 102 including the second tube connector 106. The first closing member 101a is turned toward the first tube 103 by a drive source (not shown). Moreover, the second closing member 101b is turned toward the second tube 102 by a drive source (not shown).

The first closing member 101a and the second closing member 101b are arranged on the moving portion 108. Therefore, both members move together with the moving portion 108. Alternatively, the first closing member 101a may be provided to the fixing portion 104. Moreover, the first closing member 101a and the second closing member 101b may be turned by the driving portion for the holding portions 107 (driving portion for the moving portion 108).

[Flow of Connection Operation]

Figure 2:
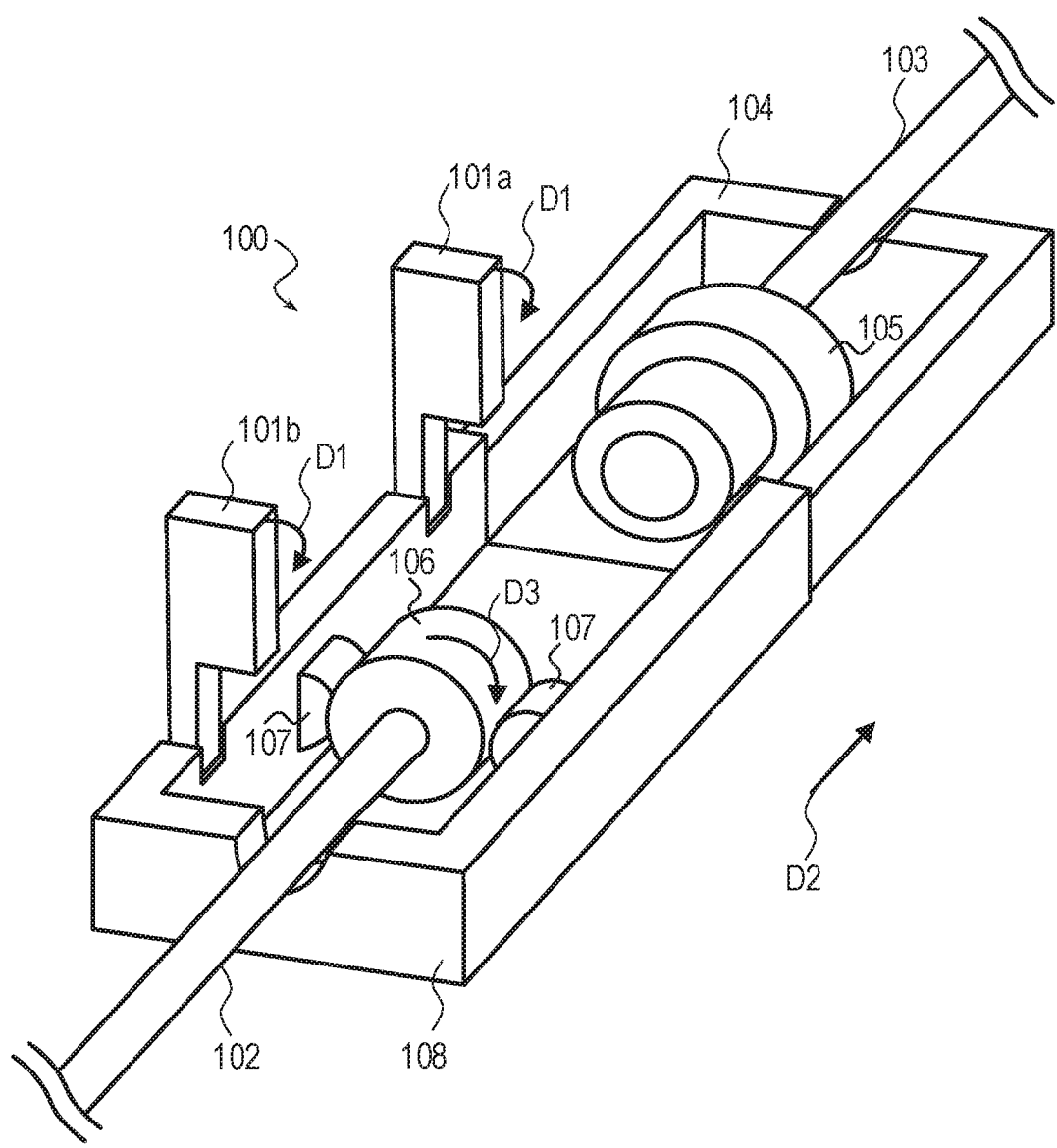
FIG. 2 is a schematic perspective view for illustrating a state before connection of flow passages in a first embodiment of the present invention.
Figure 3:
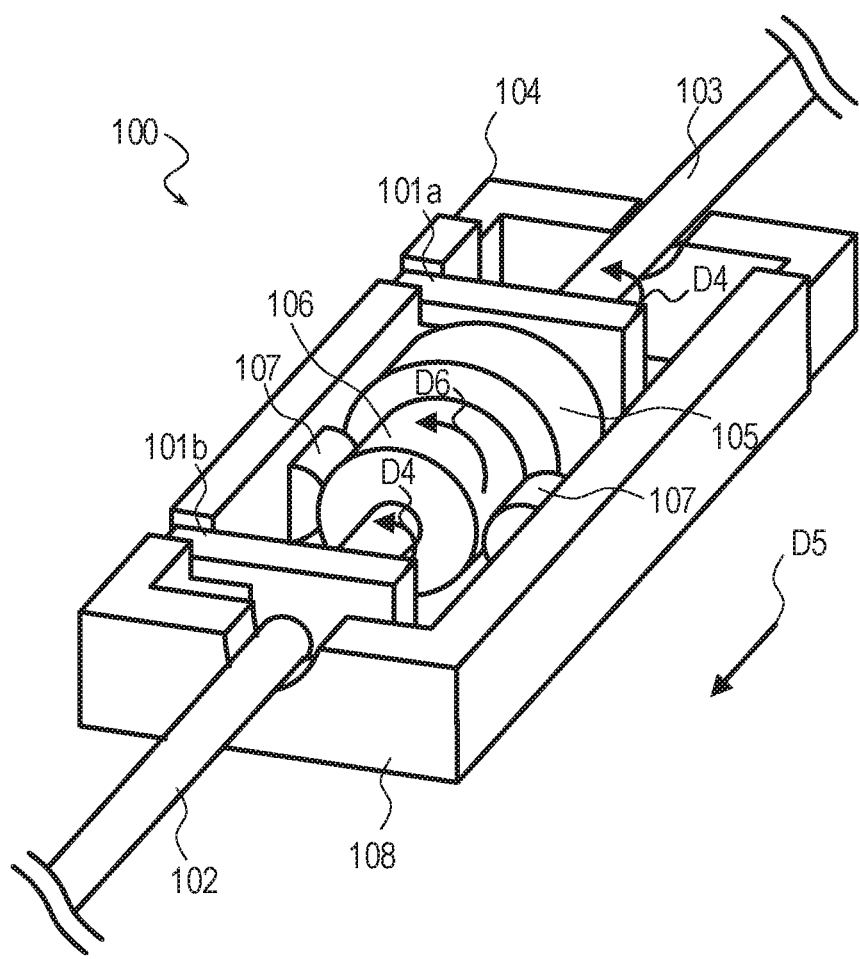
FIG. 3 is a schematic perspective view for illustrating a state after the connection of the flow passages.
Figure 4:
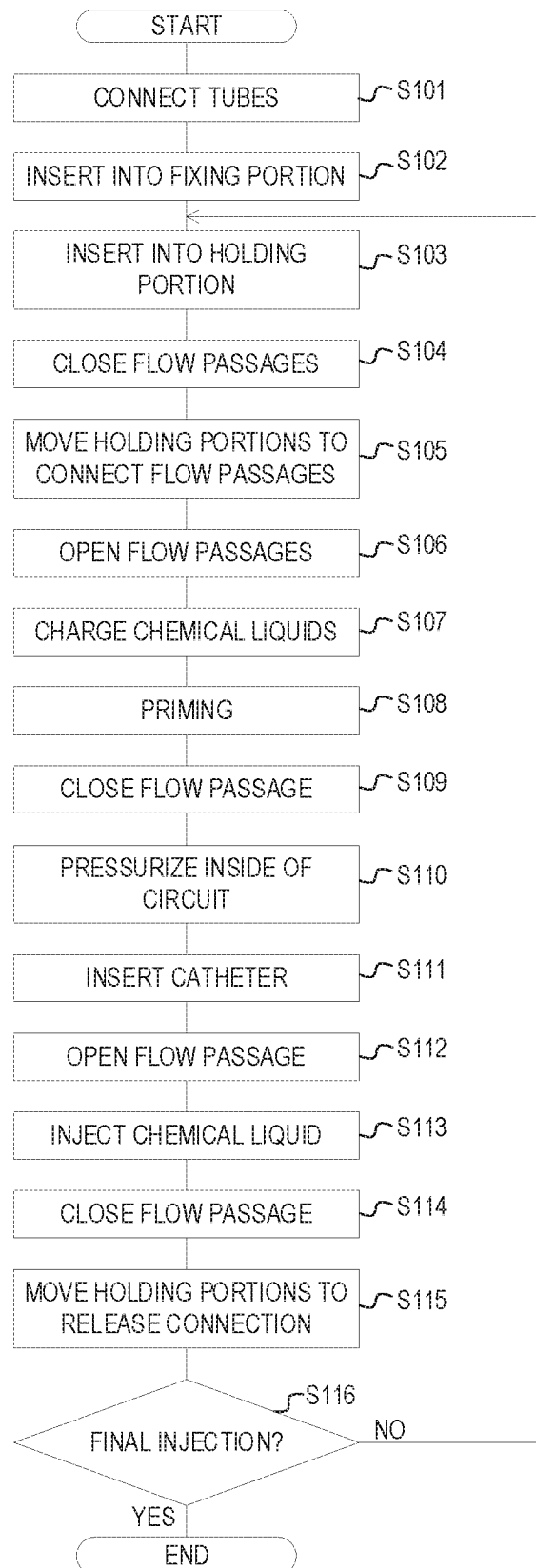
FIG. 4 is a flowchart for illustrating a connection operation for the flow passages.

A flow of a connection operation for the flow passages is described with reference to FIG. 2 to FIG. 4. FIG. 2 is an illustration of a state in which the second tube connector 106 is separated from the first tube connector 105. FIG. 3 is an illustration of a state in which the second tube connector 106 is connected to the first tube connector 105. FIG. 4 is a flowchart for illustrating the connection operation for the flow passages.

Before injection of the chemical liquid, an operator connects the contrast-medium line 501 to the contrast-medium chamber 601 and connects the physiological-saline-solution line 502 to the physiological-saline-solution chamber 602. Then, the operator connects the tubes of the contrast-medium line 501 and the physiological-saline-solution line 502 to the multi-dose injection apparatus 608 (Step S101). Next, the operator connects the first tube 103 to the contrast-medium line 501 and the physiological-saline-solution line 502 and inserts the first tube connector 105 into the fixing portion 104 (Step S102). Further, the operator connects the subject line 503 to the second tube 102 and inserts the second tube connector 106 into the holding portions 107 (Step S103).

In the direction indicated by the arrows D1 in FIG. 2, the first closing member 101a and the second closing member 101b can be turned toward the first tube 103 and the second tube 102, respectively. The multi-dose injection apparatus 608 turns the second closing member 101b to squeeze the flow passage in the second tube 102. That is, after the insertion into the fixing portion 104 and the holding portions 107 is completed, the multi-dose injection apparatus 608 automatically closes the flow passages (Step S104).

In the direction indicated by the arrow D2 in FIG. 2, the moving portion 108 is movable toward the fixing portion 104. The multi-dose injection apparatus 608 moves the moving portion 108 toward the fixing portion 104. That is, after the flow passage is closed, the multi-dose injection apparatus 608 automatically connects the flow passages (Step S105). With this configuration, the second tube connector 106 held by the holding portions 107 moves toward the first tube connector 105 fixed to the fixing portion 104.

While being moved by the moving portion 108, in the direction indicated by the arrow D3 in FIG. 2, the holding portions 107 forwardly rotate the second tube connector 106. The first tube connector 105 and the second tube connector 106 each have a thread and a thread groove. Therefore, when the second tube connector 106 is brought into contact with the first tube connector 105, both connectors threadedly engage with each other with the rotation of the second tube connector 106. With this configuration, the flow passage in the first tube 103 and the flow passage in the second tube 102 are brought into a fluid communication with each other.

In the direction indicated by the arrows D4 in FIG. 3, the first closing member 101a and the second closing member 101b can be turned so as to separate from the first tube 103 and the second tube 102, respectively. The multi-dose injection apparatus 608 turns the second closing member 101b to separate the second closing member 101b from the second tube 102. With this, the second tube 102 restores its original shape by its own elasticity, and the flow passage therein is opened. That is, after the flow passages are connected, the multi-dose injection apparatus 608 automatically opens the flow passages (Step S106).

[Priming]

Before injection of the chemical liquid, priming is performed for air drainage. Before performing the priming, the operator charges the contrast medium into the contrast-medium syringe 604 and charges the physiological saline solution into the physiological-saline-solution syringe 605 (Step S107). Specifically, the operator presses the retreat buttons 609b to allow the plungers of the contrast-medium syringe 604 and the physiological-saline-solution syringe 605 to retreat. With this, the contrast medium is charged into the contrast-medium syringe 604 through the contrast-medium line 501. Moreover, the physiological saline solution is charged into the physiological-saline solution syringe 605 through the physiological-saline-solution line 502.

Next, the operator performs a predetermined operation to perform priming through a manual operation (Step S108). Alternatively, the priming may be automatically performed by pressing down a priming button of the operation portion 609 of the multi-dose injection apparatus 608. Further, the priming may be automatically performed by the multi-dose injection apparatus 608 at a predetermined timing.

Next, when the priming is started, the operator allows the plunger of the contrast-medium syringe 604 to advance, to thereby discharge the contrast medium from the contrast-medium syringe 604. With this, the contrast medium fills, for example, the contrast-medium line 501. Alternatively, the operator may fill a region extending from the contrast-medium line 501 to the subject line 503 with the contrast medium.

Next, the operator allows the plunger of the physiological-saline-solution syringe 605 to advance, to thereby discharge the physiological saline solution from the physiological-saline-solution syringe 605. With this, the physiological saline solution fills, for example, the physiological-saline-solution line 502, the mixing device S, the first tube 103, the second tube 102, and the subject line 503. Alternatively, the operator may fill only the physiological-saline-solution line 502 with the physiological saline solution.

As a result of the priming, the entirety of the chemical liquid circuit is charged with the chemical liquids and is brought into a state in which the air is drained. Instead of discharging the contrast medium first, the operator may perform the priming by simultaneously discharging the contrast medium and the physiological saline solution. Moreover, the operator may perform the priming by discharging the physiological saline solution and thereafter discharging the contrast medium.

After the priming, the multi-dose injection apparatus 608 automatically closes the flow passage (Step S109). That is, the multi-dose injection apparatus 608 turns at least the second closing member 101b to close the flow passage in the second tube 102. Further, the multi-dose injection apparatus 608 may also turn the first closing member 101a to close the flow passage in the first tube 103.

After closing the flow passage, the multi-dose injection apparatus 608 automatically pressurizes the inside of the circuit (Step S110). That is, the multi-dose injection apparatus 608 allows the plunger of the contrast-medium syringe 604 or the plunger of the physiological-saline-solution syringe 605 to slightly advance. After that, the operator inserts the catheter into the subject (Step S111).

An internal pressure of the flow passage on an upstream side of the attaching/detaching device 100 (flow passage in the first tube 103) is higher than that of the flow passage on the downstream side of the attaching/detaching device 100 (flow passage in the second tube 102). Therefore, even when the blood backflow occurs, blood does not reach a reused portion (flow passage on the upstream side of the attaching/detaching device 100). Further, the flow passage on the downstream side of the attaching/detaching device 100 is closed by the second closing member 101b. Therefore, even when the blood backflow occurs, the blood is accumulated inside a discarded portion (second tube 102), thereby being capable of more reliably preventing contamination of the reused portion. Further, the third one-way valve V3 blocks a flow in the direction toward the reused portion, thereby being capable of more reliably preventing contamination of the reused portion.

[Injection of Chemical Liquid]

The control device for the multi-dose injection apparatus 608 includes the touch panel. When an amount of the chemical liquid and an injection protocol are determined, the control device allows the touch panel to display a predetermined piece of data or a graph. The operator checks contents displayed on the touch panel. When injection of the chemical liquid is to be started, the operator presses an enter button on the touch panel or a start button on a hand switch. Then, the control device transmits an injection command for the chemical liquid to the multi-dose injection apparatus 608.

Before injection of the chemical liquid, the multi-dose injection apparatus 608 turns the second closing member 101b to open the flow passage (Step S112). At this time, the first closing member 101a is in a flow-passage open state of being separated from the first tube 103. However, when needed, prior to the open of the flow passage of the second tube 102, the multi-dose injection apparatus 608 turns the first closing member 101a to open the flow passage.

After that, the multi-dose injection apparatus 608 allows the plunger of the contrast-medium syringe 604 to advance, to thereby discharge the contrast medium from the contrast-medium syringe 604 (Step S113). At this time, the first one-way valve V1 blocks the flow in the direction toward the contrast-medium chamber 601. Therefore, the contrast medium flows into the mixing device S through the tube of the contrast-medium line 501.

Further, when the contrast medium and the physiological saline solution are to be simultaneously injected, the multi-dose injection apparatus 608 allows the plunger of the physiological-saline-solution syringe 605 to advance, to thereby discharge the physiological saline solution from the physiological-saline-solution syringe 605. At this time, the second one-way valve V2 blocks the flow in the direction toward the physiological-saline-solution chamber 602. Therefore, the physiological saline solution flows into the mixing device S through the tube of the physiological-saline-solution line 502. With this, the contrast medium and the physiological saline solution flow into the mixing device S and are mixed in the mixing device S.

A mixed chemical liquid of the contrast medium and the physiological saline solution is injected into a predetermined imaged part through the subject line 503 and the catheter. After injection of the contrast medium is completed, the multi-dose injection apparatus 608 allows the plunger of the physiological-saline-solution syringe 605 to advance, to thereby discharge the physiological saline solution from the physiological-saline-solution syringe 605. Then, the physiological saline solution is injected into the predetermined imaged part through the tube of the physiological-saline-solution line 502, the subject line 503, and the catheter. With this, flushing of the contrast medium with the physiological saline solution is performed.

When the amount of the contrast medium in the contrast-medium syringe 604 becomes smaller than a predetermined amount, the multi-dose injection apparatus 608 performs suction of the contrast medium. That is, the multi-dose injection apparatus 608 allows the plunger of the contrast-medium syringe 604 to retreat, to thereby suck the contrast medium from the contrast-medium chamber 601 toward the contrast-medium syringe 604. At this time, the first one-way valve V1 permits the flow in the direction toward the contrast-medium syringe 604. Moreover, before the suction of the contrast medium, the multi-dose injection apparatus 608 turns the first closing member 101a and the second closing member 101b to close the flow passages.

When the amount of the physiological saline solution in the physiological-saline-solution syringe 605 becomes smaller than a predetermined amount, the multi-dose injection apparatus 608 performs suction of the physiological saline solution. That is, the multi-dose injection apparatus 608 allows the plunger of the physiological-saline-solution syringe 605 to retreat, to thereby suck the physiological saline solution from the physiological-saline-solution chamber 602 toward the physiological-saline-solution syringe 605. At this time, the second one-way valve V2 permits the flow in the direction toward the physiological-saline-solution syringe 605. Moreover, before the suction of the physiological saline solution, the multi-dose injection apparatus 608 turns the first closing member 101a and the second closing member 101b to close the flow passages.

After the suction, the multi-dose injection apparatus 608 turns the first closing member 101a and the second closing member 101b to open the flow passages. Then, the multi-dose injection apparatus 608 allows the plunger of the contrast-medium syringe 604 to advance, thereby being capable of discharging the sucked contrast medium toward the subject line 503. Similarly, the multi-dose injection apparatus 608 allows the plunger of the physiological-saline-solution syringe 605 to advance, thereby being capable of discharging the sucked physiological saline solution toward the subject line 503.

After the injection of the chemical liquid is completed, the multi-dose injection apparatus 608 automatically closes the flow passage (Step S114). That is, the multi-dose injection apparatus 608 turns the second closing member 101b to close the flow passage in the second tube 102. At this time, the first closing member 101a is in a flow-passage open state of being separated from the first tube 103.

In the direction indicated by the arrow D5 in FIG. 3, the moving portion 108 is movable in the direction of separating from the fixing portion 104. The multi-dose injection apparatus 608 separates the moving portion 108 from the fixing portion 104. That is, the multi-dose injection apparatus 608 automatically releases the connection of the flow passages after closing the flow passage in the second tube 102 (Step S115). With this, the second tube connector 106 held by the holding portions 107 is separated from the first tube connector 105 fixed to the fixing portion 104.

While being moved by the moving portion 108, in the direction indicated by the arrow D6 in FIG. 3, the holding portions 107 reversely rotate the second tube connector 106. Therefore, the second tube connector 106 is disengaged with the reverse rotation, and the threaded engagement of the first tube connector 105 and the second tube connector 106 is released. Then, the connection of the flow passage in the first tube 103 and the flow passage in the second tube 102 is released. With this, the flow passages are separated. Thus, even when the blood backflow occurs, blood does not reach the reused portion, thereby being capable of more reliably preventing the contamination of the reused portion.

After that, the multi-dose injection apparatus 608 determines whether final injection has been completed (Step S116). When the final injection has been completed, (YES in Step S116), that is, when injection to the last subject has been completed, the operation is terminated. When the final injection has not been completed (NO in Step S116), that is, when the next injection to a subject is to be performed, the routine returns to Step S103, and the operation is continued.

Specifically, the operator removes the used second tube 102 and the used subject line 503. Next, the operator connects a subject line 503 to a second tube 102 and inserts the second tube connector 106 into the holding portions 107 (Step S103). Then, next injection into a subject is performed.

[Sensor]

As illustrated in FIG. 1, the multi-dose injection apparatus 608 includes a sensor 530 which is provided so as to be opposed to the first tube 103 including the first tube connector 105. The sensor 530 is configured to detect air inside the first tube 103 or detect a flow of the chemical liquid inside the first tube 103. Further, the multi-dose injection apparatus 608 may include a sensor 530 which is provided so as to be opposed to the second tube 102 including the second tube connector 106.

The sensor 530 transmits a signal to the multi-dose injection apparatus 608 when the presence of air bubbles is detected. The multi-dose injection apparatus 608 having received the signal performs at least one of stopping the injection of the chemical liquid and giving notification (alert) with regard to the detection of air. Alternatively, the sensor 530 transmits a signal to the multi-dose injection apparatus 608 when a flow of the chemical liquid is no longer detected. The multi-dose injection apparatus 608 having received the signal determines that the injection of the chemical liquid has been stopped. In order to prevent the contamination caused by the blood backflow, the multi-dose injection apparatus 608 closes the flow passages in the first tube 103 and the second tube 102. Alternatively, the multi-dose injection apparatus 608 moves the moving portion 108 to release the connection of the flow passages.

The sensor 530 is, for example, an ultrasonic sensor or an optical sensor (for example, infrared sensor). Further, the sensor 530 may be provided at a position opposed to a tube of the contrast-medium line 501, the physiological-saline-solution line 502, or the subject line 503. Moreover, the sensor 530 may be a temperature sensor configured to detect a temperature of the chemical liquid. Air bubbles have a thermal conductivity lower than that of the chemical liquid, and hence the control device for the multi-dose injection apparatus 608 is capable of determining the presence of air bubbles by monitoring a change in the detected temperature.

According to the injection system 500 of the first embodiment described above, the first tube connector 105 and the second tube connector 106 are automatically and mechanically attachable and detachable. Thus, the connection work for the flow passages can easily be performed. Moreover, the first tube connector 105 and the second tube connector 106 are physically separated from each other immediately after injection of the chemical liquid. Therefore, even when the blood backflow occurs, contamination on the upstream side of the attaching/detaching device 100 (injection apparatus side) can be prevented.

The syringes mounted to the multi-dose injection apparatus 608 may each be any one of a syringe having a chemical liquid charged therein or an empty syringe having no chemical liquid charged therein. Examples of the syringe having a chemical liquid charged therein include a pre-filled syringe having a chemical liquid charged therein in advance, a syringe obtained by charging a chemical liquid into an empty syringe with a suction device or a charge device operated by an operator, and a syringe obtained by charging a chemical liquid into an empty syringe through a manual operation by an operator. Further, contrast media having different concentrations may be charged in the two syringes mounted to the multi-dose injection apparatus 608. Moreover, a mixed chemical liquid of a contrast medium and a physiological saline solution may be charged in at least one of the two syringes.

Second Embodiment

With reference to FIG. 5 to FIG. 8, a second embodiment is described. Unlike the first embodiment, an attaching/detaching device 200 according to the second embodiment includes a removing member 221. The removing member 221 is configured to remove at least one of a first cap 222a mounted to the first tube connector 105 and a second cap 222b mounted to the second tube connector 106. In the description of the second embodiment, points different from the first embodiment are described, and a description of components described in the first embodiment is omitted. Unless otherwise particularly described, components denoted by the same reference symbols have the same operations and functions, and actions and effects are also substantially the same.

Figure 5:
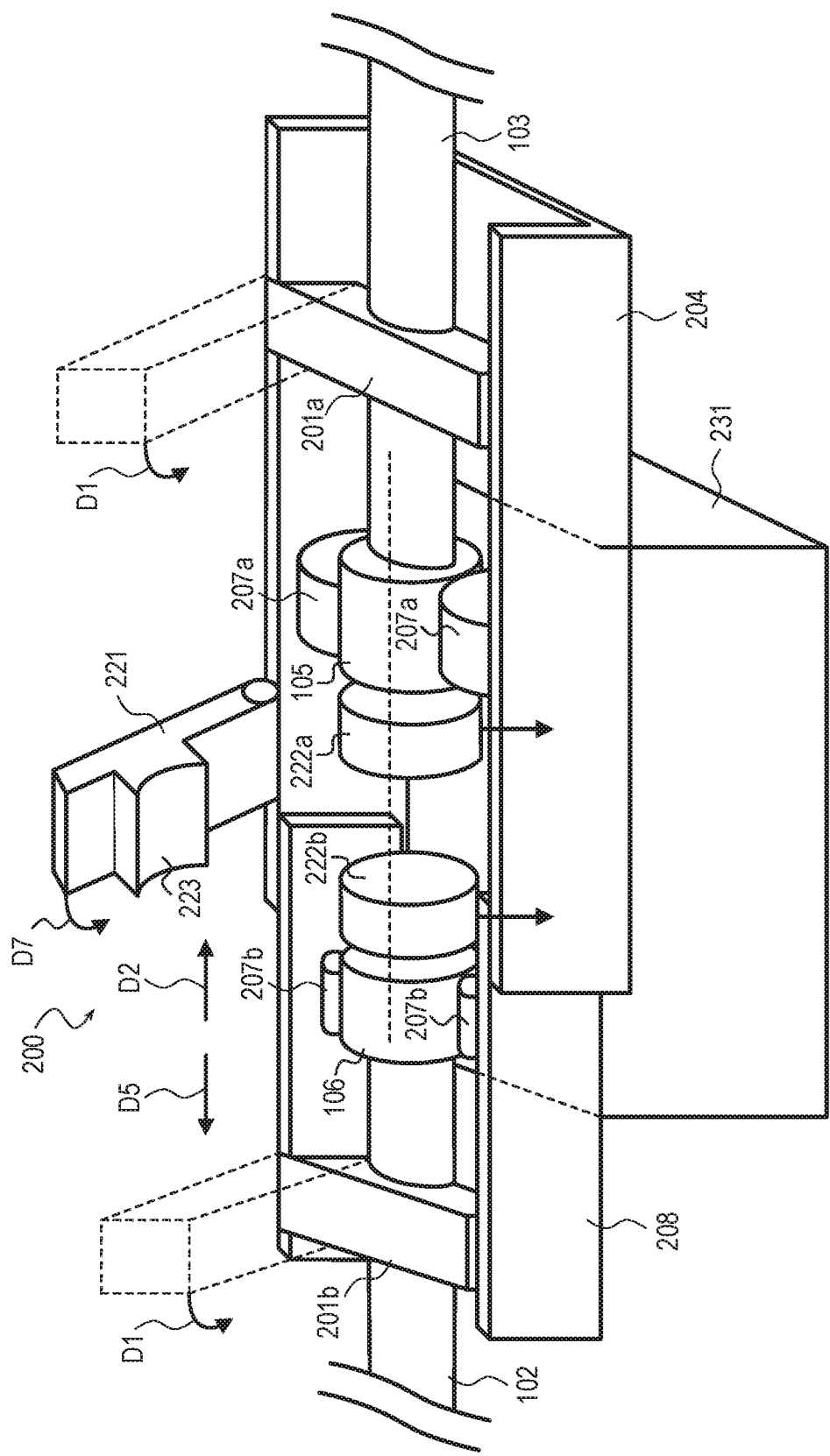
FIG. 5 is a schematic perspective view for illustrating a state before connection of flow passages in a second embodiment of the present invention.

FIG. 5 is a schematic perspective view for illustrating the attaching/detaching device 200 in which the flow passages are closed, and is an illustration of a state in which the second tube connector 106 is separated from the first tube connector 105. The attaching/detaching device 200 includes a fixing portion 204 and holding portions 207a. The fixing portion 204 is configured to fix the first tube connector 105. The holding portions 207a are configured to hold the first tube connector 105. Moreover, the attaching/detaching device 200 includes holding portions 207b. The holding portions 207b are configured to hold the second tube connector 106. Further, the attaching/detaching device 200 includes a moving portion 208. The moving portion 208 is capable of moving the holding portions 207b, which hold the second tube connector 106, in the direction of approaching the first tube connector 105 and in the direction of separating from the first tube connector 105.

The first cap 222a is mounted to the first tube connector 105, and the second cap 222b is mounted to the second tube connector 106. The attaching/detaching device 200 includes the removing member 221 configured to strike down the first cap 222a and the second cap 222b. The removing member 221 is turned by a drive source (not shown) in the direction indicated by the arrow D7 in FIG. 5. Further, the removing member 221 includes a projecting portion 223 projecting outward. The projecting portion 223 has, at a center portion thereof, a recess portion extending in a width direction. The recess portion has a U-shaped cross section, but may have a V-shaped cross section. Further, the recess portion may extend in a longitudinal direction. In this case, both end portions of the recess portion extending in the longitudinal direction strike the first cap 222a and the second cap 222b, respectively.

The attaching/detaching device 200 includes a collection box 231 configured to collect the first cap 222a and the second cap 222b. The fixing portion 204 and the moving portion 208 have openings formed in respective bottom surfaces so as to communicate with the collection box 231. Therefore, the first cap 222a and the second cap 222b having been struck down by the removing member 221 fall into the collection box 231. Moreover, the collection box 231 is removable from the attaching/detaching device 200. An operator can discard the first cap 222a and the second cap 222b having been removed and collected in the collection box 231.

The moving portion 208 is located on an inner side of the fixing portion 204. The moving portion 208 moves in the direction indicated by the arrow D2 or the arrow D5 in FIG. 5 after removal of the first cap 222a and the second cap 222b. With the movement of the moving portion 208, an end portion of the moving portion 208 slides on the inner side of the fixing portion 204.

A pair of fingers serving as the holding portions 207b forwardly rotate while the moving portion 208 moves in the direction of approaching the fixing portion 204. With this, the second tube connector 106 is forwardly rotated by the pair of fingers to be brought into contact and threaded engagement with the first tube connector 105. Meanwhile, the pair of fingers reversely rotate while the moving portion 208 moves in the direction of separating from the fixing portion 204. With this, the second tube connector 106 is reversely rotated by the pair of fingers to be disengaged and separated from the first tube connector 105.

Further, the attaching/detaching device 200 includes a first closing member 201a and a second closing member 201b. The first closing member 201a is configured to close the first tube 103 including the first tube connector 105. The second closing member 201b is configured to close the second tube 102 including the second tube connector 106. The first closing member 201a is provided on the moving portion 208, and the second closing member 201b is provided on the fixing portion 204. The first closing member 201a and the second closing member 201b turn in the direction indicated by the arrows D1 in FIG. 5, respectively.

[Flow of Connection Operation]

Figure 6:
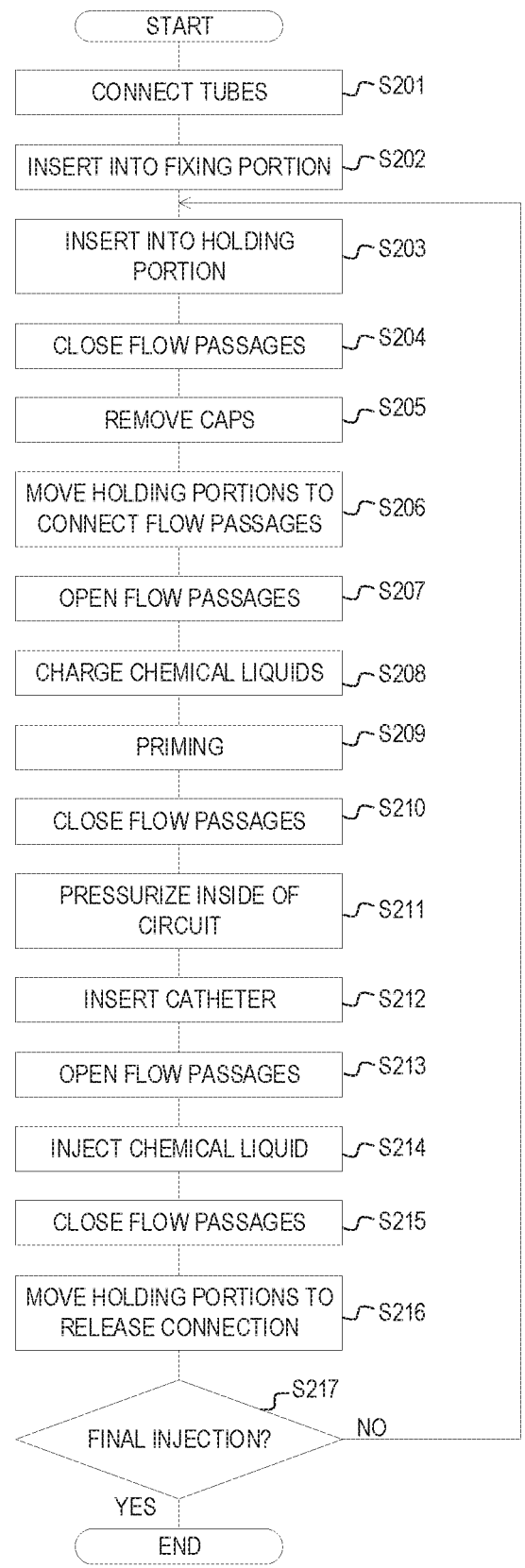
FIG. 6 is a flowchart for illustrating a connection operation for the flow passages.
Figure 7:
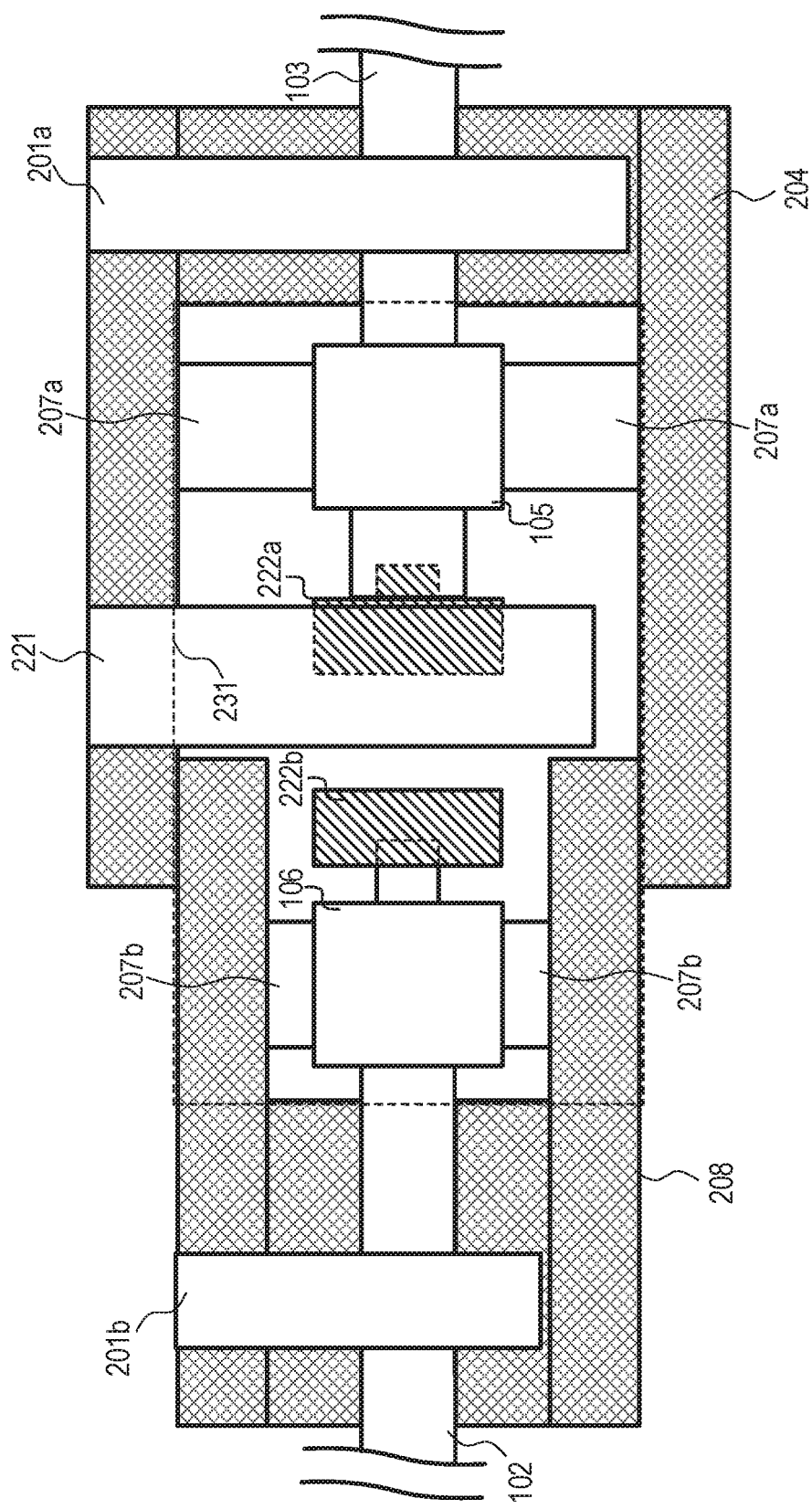
FIG. 7 is a schematic top view for illustrating a state of striking down a first cap.
Figure 8:
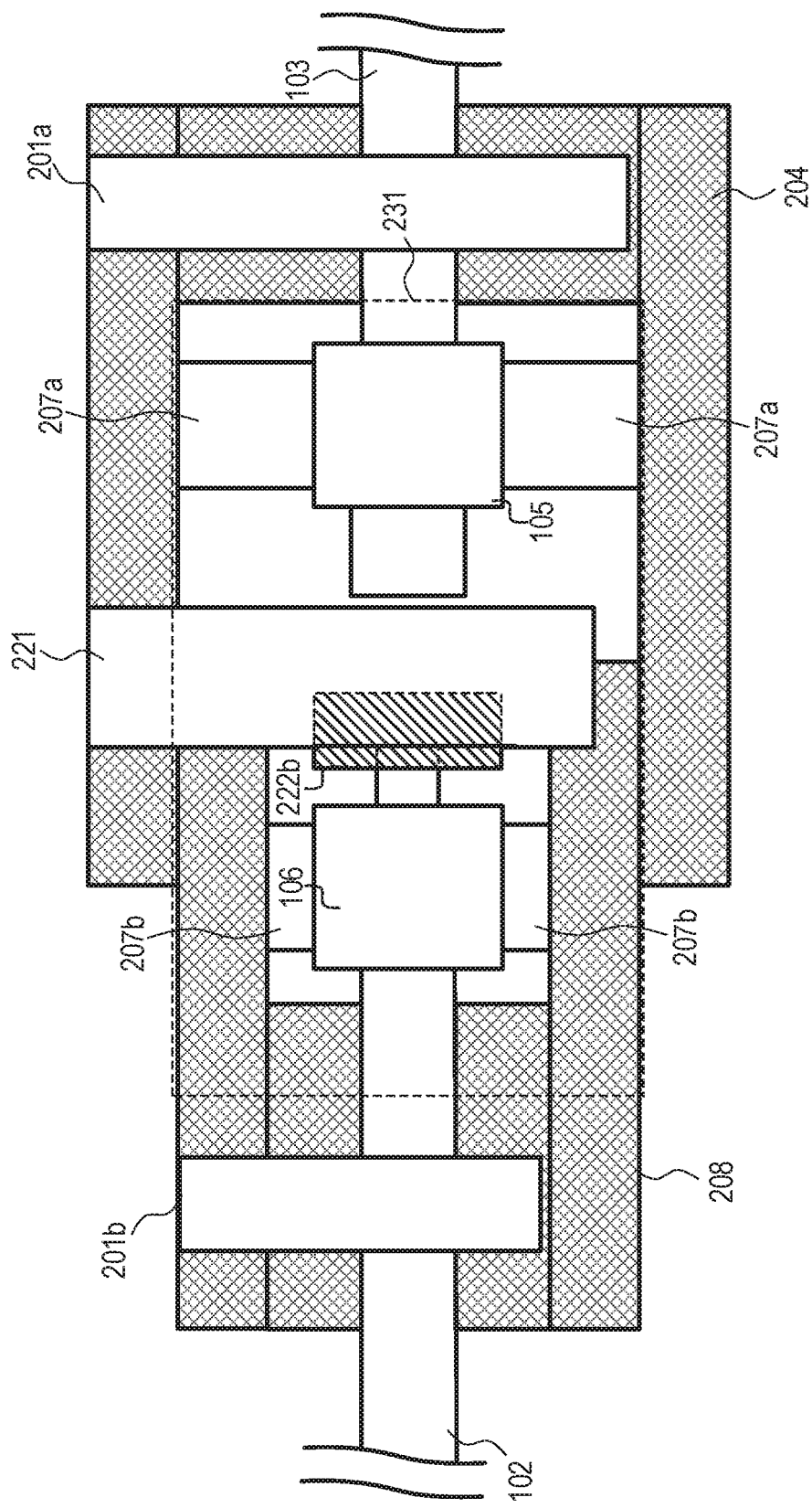
FIG. 8 is a schematic top view for illustrating a state of striking down a second cap.

A flow of a connection operation for the flow passages is described with reference to FIG. 6 to FIG. 8. FIG. 6 is a flowchart for illustrating the connection operation for the flow passages. FIG. 7 is an illustration of a state in which the first cap 222a is struck down. FIG. 8 is an illustration of a state in which the second cap 222b is struck down. In FIG. 7 and FIG. 8, an outer shape of the collection box 231 which cannot be visually recognized from above is illustrated with dotted lines. Moreover, portions of the first cap 222a and the second cap 222b which cannot be visually recognized from above are illustrated with dotted lines.

Before injection of the chemical liquid, an operator connects the contrast-medium line 501 to the contrast-medium chamber 601 and connects the physiological-saline-solution line 502 to the physiological-saline-solution chamber 602. Then, the operator connects the tubes of the contrast-medium line 501 and the physiological-saline-solution line 502 to the multi-dose injection apparatus 608 (Step S201). Next, the operator connects to the first tube 103 to the contrast-medium line 501 and the physiological-saline-solution line 502 and inserts the first tube connector 105 into the fixing portion 204 (Step S202). Further, the operator connects the subject line 503 to the second tube 102 and inserts the second tube connector 106 into the holding portions 207b (Step S203).

Next, the multi-dose injection apparatus 608 turns the first closing member 201a and the second closing member 201b to automatically close the flow passages (Step S204). After closing the flow passages, the multi-dose injection apparatus 608 automatically removes the caps (Step S205). That is, the multi-dose injection apparatus 608 turns the removing member 221 to cause the first cap 222a and the second cap 222b to fall into the collection box 231. Removal of the caps is more specifically described with reference to FIG. 7 and FIG. 8.

First, the multi-dose injection apparatus 608 turns the removing member 221 to cause the removing member 221 to strike the first cap 222a (FIG. 7). The first cap 222a is removed from the first tube connector 105 due to the impact of the strike and falls into the collection box 231. Then, the multi-dose injection apparatus 608 turns the removing member 221 to move the removing member 221 to an original position (initial position). After that, the multi-dose injection apparatus 608 moves the moving portion 208 toward the fixing portion 204. Then, the multi-dose injection apparatus 608 turns the removing member 221 again to cause the removing member 221 to strike the second cap 222b (FIG. 8). The second cap 222b is removed from the second tube connector 106 due to the impact of the strike and falls into the collection box 231. Then, the multi-dose injection apparatus 608 turns the removing member 221 to move the removing member 221 to the original position (initial position).

After that, the multi-dose injection apparatus 608 moves the moving portion 208 toward the fixing portion 204 to automatically connect the flow passages (Step S206). With this, the flow passage in the first tube 103 and the flow passage in the second tube 102 are brought into a fluid communication with each other. Then, the multi-dose injection apparatus 608 turns the first closing member 201a and the second closing member 201b to automatically open the flow passages (Step S207).

Next, the operator charges the contrast medium into the contrast-medium syringe 604 and charges the physiological saline solution into the physiological-saline-solution syringe 605 (Step S208), and then performs priming (S209). After the priming, the multi-dose injection apparatus 608 turns the first closing member 201a and the second closing member 201b to automatically close the flow passages (Step S210). After closing the flow passages, the multi-dose injection apparatus 608 automatically pressurizes the inside of the circuit (Step S211). Alternatively, the multi-dose injection apparatus 608 may close the flow passages while pressurizing the inside of the circuit. After that, the operator inserts the catheter into a subject (Step S212). The operations of charging the contrast medium and the physiological saline solution may be performed at freely selected timings after the tubes of the contrast-medium line 501 and the physiological-saline-solution line 502 are connected to the multi-dose injection apparatus 608 (Step S201).

Before the injection of the chemical liquid, the multi-dose injection apparatus 608 turns the second closing member 201b and the first closing member 201a to open the flow passages (Step S213). After that, the multi-dose injection apparatus 608 discharges the contrast medium from the contrast-medium syringe 604 (Step S214). When the contrast medium and the physiological saline solution are to be simultaneously injected, the multi-dose injection apparatus 608 discharges the physiological saline solution also from the physiological-saline-solution syringe 605. With this, the contrast medium and the physiological saline solution flow into the mixing device S and are mixed in the mixing device S.

After the injection of the chemical liquid is completed, the multi-dose injection apparatus 608 turns the first closing member 201a and the second closing member 201b to automatically close the flow passages (Step S215). Then, the multi-dose injection apparatus 608 separates the moving portion 208 from the fixing portion 204 to automatically release the connection of the flow passages (Step S216). After that, the multi-dose injection apparatus 608 determines whether the final injection has been completed (Step S217). When the final injection has been completed (YES in Step S217), that is, when injection to the last subject has been completed, the operation is terminated. When the final injection has not been completed (NO in Step S217), that is, the next injection to another subject is to be performed, the routine returns to Step S203, and the operation is continued.

With the injection system 500 according to the second embodiment described above, the first tube connector 105 and the second tube connector 106 are automatically and mechanically attachable and detachable. Thus, the connection work for the flow passages can easily be performed. Moreover, the first tube connector 105 and the second tube connector 106 are physically separated from each other immediately after the injection of the chemical liquid. Therefore, even when the blood backflow occurs, contamination on the upstream side of the attaching/detaching device 200 (injection apparatus side) can be prevented.

Further, with the attaching/detaching device 200 according to the second embodiment, the first tube connector 105 and the second tube connector 106 are sealed with the first cap 222a and the second cap 222b, respectively. With this, the contamination of the first tube connector 105 and the second tube connector 106 can be prevented.

Third Embodiment

A third embodiment is described with reference to FIG. 9. Unlike the second embodiment, an attaching/detaching device 300 according to the third embodiment includes first removing members 321a and second removing members 321b. The first removing members 321a are configured to rotate the first cap 222a to remove the first cap 222a. The second removing members 321b are configured to rotate the second cap 222b to remove the second cap 222b. In the description of the third embodiment, points different from the first and second embodiment are described, and a description of components described in the first and second embodiment is omitted. Unless otherwise particularly described, components denoted by the same reference symbols have the same operations and functions, and actions and effects are also substantially the same.

Figure 9:
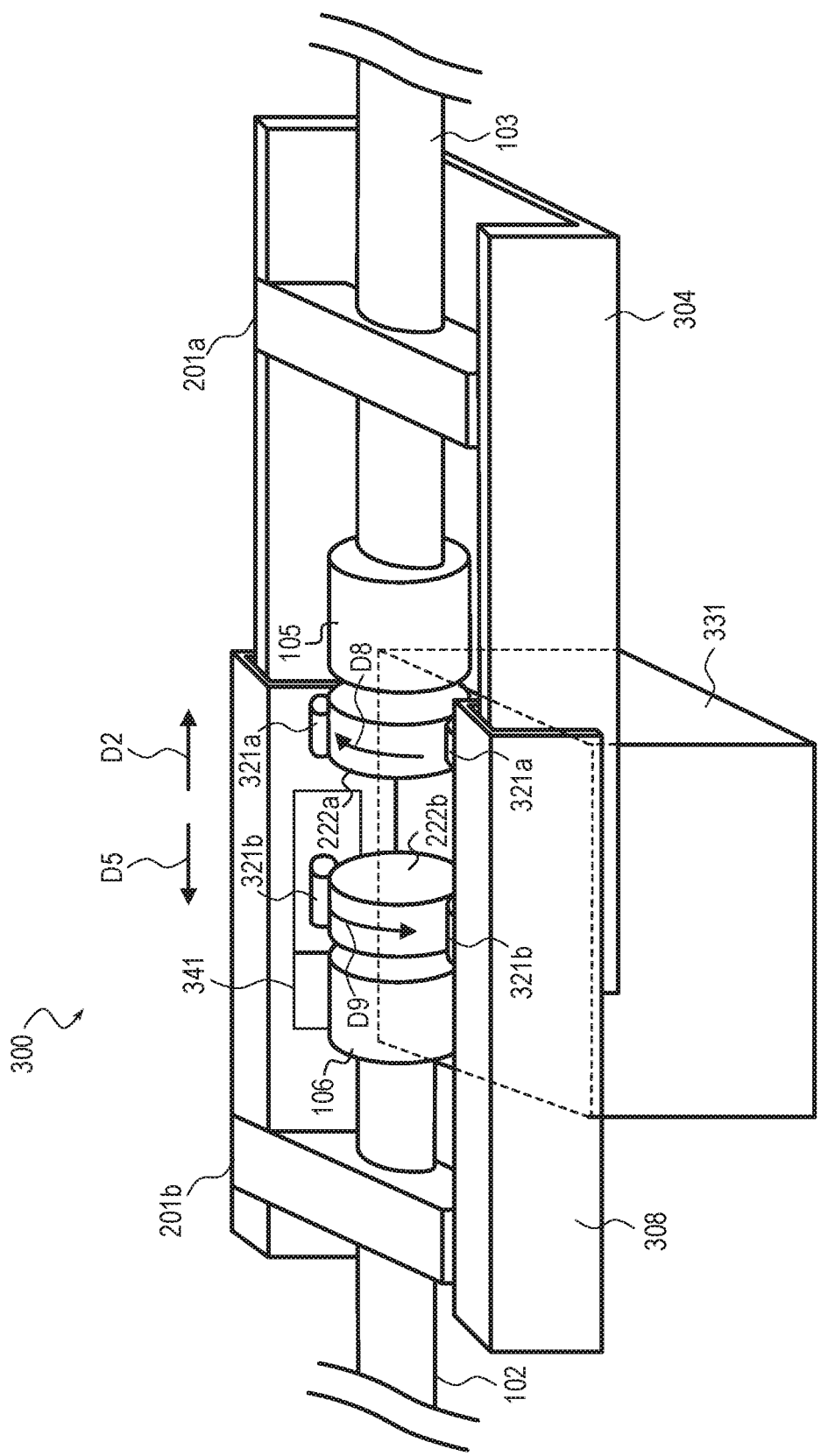
FIG. 9 is a schematic perspective view for illustrating a state before connection of flow passages in a third embodiment of the present invention.

FIG. 9 is a schematic perspective view for illustrating the attaching/detaching device 300 in which the flow passages are closed, and is an illustration of a state in which the second tube connector 106 is separated from the first tube connector 105. The attaching/detaching device 300 includes a fixing portion 304 configured to fix the first tube connector 105, and the first tube connector 105 is held by a slot (not shown). Moreover, the attaching/detaching device 300 includes the second removing members 321b which function also as holding portions configured to hold the second tube connector 106. Further, the attaching/detaching device 300 includes a moving portion 308. The moving portion 308 is capable of moving the second removing members 321b, which hold the second tube connector 106, in the direction of approaching the first tube connector 105 and in the direction of separating from the first tube connector 105.

The first cap 222a is threadedly engaged with the first tube connector 105, and the second cap 222b is threadedly engaged with the second tube connector 106. The attaching/detaching device 300 includes the first removing members 321a, which are configured to rotate the first cap 222a, and the second removing members 321b, which are configured to rotate the second cap 222b. The first removing members 321a are a pair of substantially roller-shaped members, and the second removing members 321b are a pair of substantially roller-shaped members. The first removing members 321a and the second removing members 321b are each driven by a drive source (not shown) to rotate the first cap 222a and the second cap 222b in the directions indicated by the arrows D8 and D9 in FIG. 9, respectively.

The attaching/detaching device 300 includes a collection box 331 configured to collect the first cap 222a and the second cap 222b. The fixing portion 304 and the moving portion 308 have openings formed in respective bottom surfaces so as to communicate with the collection box 331. Therefore, the first cap 222a and the second cap 222b having been removed by the first removing member 321a and the second removing member 321b fall into the collection box 331. Moreover, the collection box 331 is removable from the attaching/detaching device 300. An operator can discard the first cap 222a and the second cap 222b having been removed and collected in the collection box 331. A slot for fixing the first tube connector 105 is formed in the bottom surface of the fixing portion 304, and hence the collection box 331 of the third embodiment is smaller than that of the second embodiment.

Removal of the caps is more specifically described. First, the multi-dose injection apparatus 608 rotates the first removing members 321a to rotate the first cap 222a in the direction indicated by the arrow D8 in FIG. 9. The first cap 222a having been released from the threaded engagement by the rotation is removed from the first tube connector 105 and falls into the collection box 331. At the same time, the multi-dose injection apparatus 608 rotates the second removing members 321b to rotate the second cap 222b in the direction indicated by the arrow D9 in FIG. 9. The second cap 222b having been released from the threaded engagement by the rotation is removed from the second tube connector 106 and falls into the collection box 331.

After that, the multi-dose injection apparatus 608 moves the moving portion 308 toward the fixing portion 304 to cause the second tube connector 106 to be held by the second removing members 321b. The moving portion 308 has rectangular slits 341 formed so as not to hinder the movement of the second removing members 321b. Therefore, the second removing members 321b move in the direction indicated by the arrow D5 or D2 of FIG. 9 in the slits 341 with the movement of the moving portion 308.

Both end portions of the moving portion 308 are each a member having a substantially U-shaped cross section and cover upper portions of the fixing portion 304. The moving portion 308 moves in the direction indicated by the arrow D2 or D5 in FIG. 9 after the removal of the first cap 222a and the second cap 222b. Then, as the moving portion 308 moves relative to the fixing portion 304, the both end portions of the fixing portion 304 are received in the moving portion 308. Moreover, as the moving portion 308 separates from the fixing portion 304, the both end portions of the fixing portion 304 are exposed from the moving portion 308.

The second removing members 321b forwardly rotate while the moving portion 308 moves in the direction of approaching the fixing portion 304. With this, the second tube connector 106 is forwardly rotated by the pair of fingers to be brought into contact and threaded engagement with the first tube connector 105. Meanwhile, the pair of fingers reversely rotate while the moving portion 308 moves in the direction of separating from the fixing portion 304. With this, the second tube connector 106 is reversely rotated by the pair of fingers to be disengaged and separated from the first tube connector 105.

Further, the attaching/detaching device 300 includes the first closing member 201a, which is configured to close the first tube 103 including the first tube connector 105, and the second closing member 201b, which is configured to close the second tube 102 including the second tube connector 106. The first closing member 201a is provided on the fixing portion 304, and the second closing member 201b is provided on the moving portion 308. The first closing member 201a and the second closing member 201b turn toward the first tube connector 105 and the second tube connector 106, respectively.

With the injection system 500 according to the third embodiment described above, the first tube connector 105 and the second tube connector 106 are automatically and mechanically attachable and detachable. Thus, the connection work for the flow passages can easily be performed. Moreover, the first tube connector 105 and the second tube connector 106 are physically separated from each other immediately after the injection of the chemical liquid. Therefore, even when the blood backflow occurs, contamination on the upstream side of the attaching/detaching device 300 (injection apparatus side) can be prevented.

Further, with the attaching/detaching device 300 according to the third embodiment, the first tube connector 105 and the second tube connector 106 are sealed with the first cap 222a and the second cap 222b, respectively. With this, the contamination of the first tube connector 105 and the second tube connector 106 can be prevented.

Fourth Embodiment

A fourth embodiment is described with reference to FIG. 10. An attaching/detaching device 400 according to the fourth embodiment includes a cartridge 440 configured to accommodate a plurality of second tube connectors 106. In the description of the fourth embodiment, points different from the first and second embodiment are described, and a description of components described in the first and second embodiment is omitted. Unless otherwise particularly described, components denoted by the same reference symbols have the same operations and functions, and actions and effects are also substantially the same.

Figure 10:
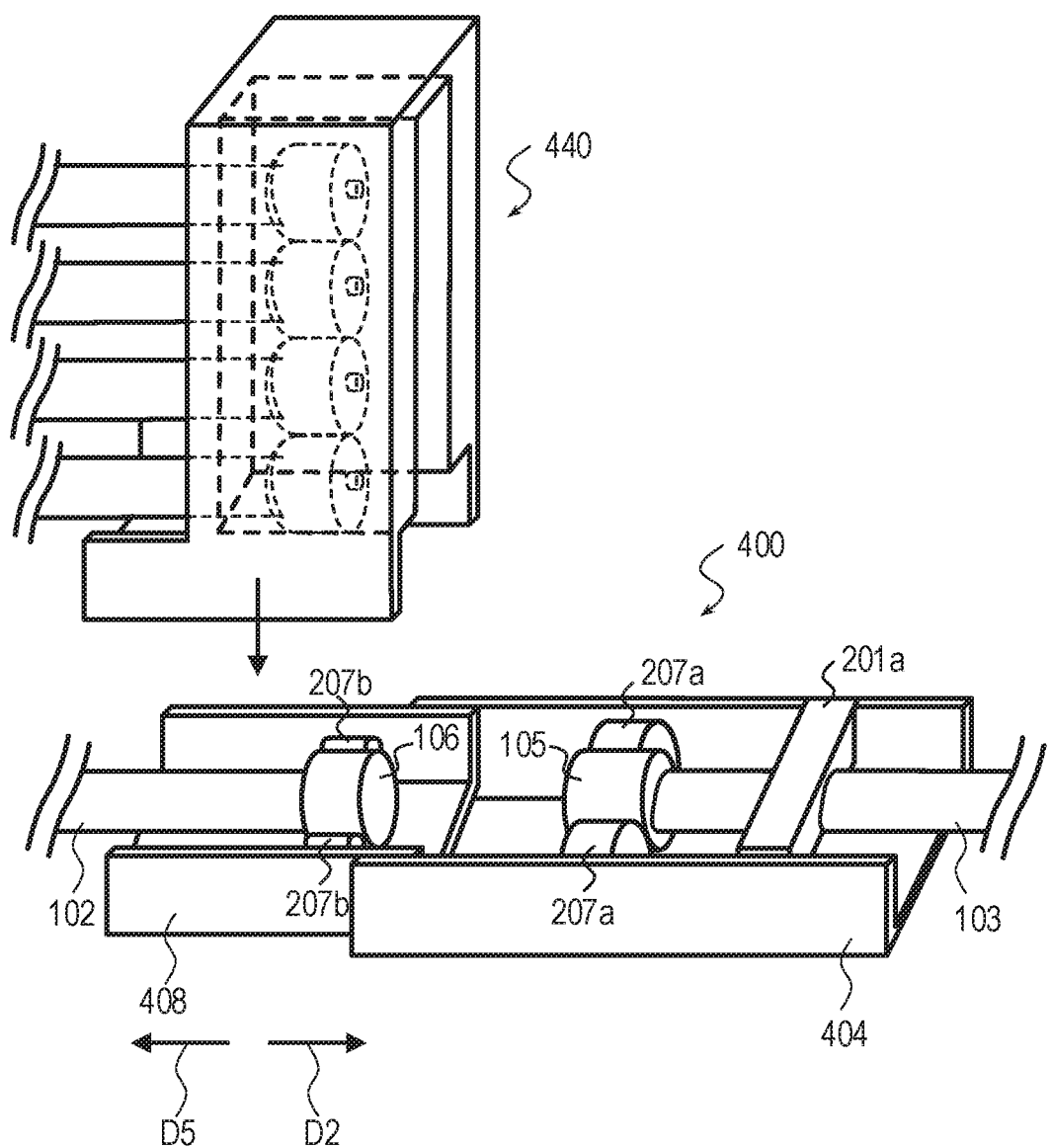
FIG. 10 is a schematic perspective view for illustrating a state before connection of flow passages in a fourth embodiment of the present invention.

FIG. 10 is a schematic perspective view for illustrating the attaching/detaching device 400 in which the flow passages are closed, and is an illustration of a state in which the second tube connector 106 is separated from the first tube connector 105. The attaching/detaching device 400 includes a fixing portion 404 and the holding portions 207a. The fixing portion 404 is configured to fix the first tube connector 105. The holding portions 207a are configured to hold the first tube connector 105. Moreover, the attaching/detaching device 400 includes the holding portions 207b. The holding portions 207b are configured to hold the second tube connector 106.

Further, the attaching/detaching device 400 includes a moving portion 408. The moving portion 408 is capable of moving the holding portions 207b, which hold the second tube connector 106, in the direction of approaching the first tube connector 105 and in the direction of separating from the first tube connector 105. The moving portion 408 has a substantially U-shaped cross section and is located on an inner side of the fixing portion 404. The moving portion 408 moves in the direction indicated by the arrow D2 or the arrow D5 in FIG. 10. An end portion of the moving portion 408 slides on the inner side of the fixing portion 404 with the movement of the moving portion 408.

The pair of fingers serving as the holding portions 207b forwardly rotate while the moving portion 408 moves in the direction of approaching the fixing portion 404. With this, the second tube connector 106 is forwardly rotated by the pair of fingers to be brought into contact and threaded engagement with the first tube connector 105. Meanwhile, the pair of fingers reversely rotate while the moving portion 408 moves in the direction of separating from the fixing portion 404. With this, the second tube connector 106 is reversely rotated by the pair of fingers to be disengaged and separated from the first tube connector 105.

Moreover, the attaching/detaching device 400 includes the first closing member 201a configured to close first tube 103 including the first tube connector 105. The first closing member 201a is provided on the fixing portion 404 so as to be turnable. Further, the attaching/detaching device 400 includes the cartridge 440, which is configured to accommodate the plurality of second tube connectors 106 and second tubes 102 and is attachable to and detachable from the attaching/detaching device 400. A slit is formed in each of a front surface and a rear surface of a casing of the cartridge 440. After the injection of the chemical liquid is terminated, an operator can mount the second tube connector 106 and the second tube 102 inside the cartridge 440 to the attaching/detaching device 400.

More specifically, before injection of the chemical liquid, an operator mounts the cartridge 440 to the attaching/detaching device 400. After the injection of the chemical liquid is terminated, the operator pulls out the second tube connector 106 and the second tube 102, which have been used, from the attaching/detaching device 400. Next, the operator presses down the second tube connector 106 and the second tube 102 through the slits of the cartridge 440.

At this time, the operator presses down the second tube connector 106 and the second tube 102 to a position at which the second tube connector 106 is held by the holding portions 207b. With this, the second tube connector 106 and the second tube 102 are mounted to the attaching/detaching device 400. After that, the operator restarts injection of the chemical liquid. Then, after the re-injection of the chemical liquid is terminated, the operator pulls out the second tube connector 106 and the second tube 102, which have been used, from the attaching/detaching device 400 and replace the second tube connector 106 and the second tube 102 with a new second tube connector 106 and a new second tube 102.

With the injection system 500 according to the fourth embodiment described above, the first tube connector 105 and the second tube connector 106 are automatically and mechanically attachable and detachable. Thus, the connection work for the flow passages can easily be performed. Moreover, the first tube connector 105 and the second tube connector 106 are physically separated from each other immediately after the injection of the chemical liquid. Therefore, even when the blood backflow occurs, contamination on the upstream side of the attaching/detaching device 400 (injection apparatus side) can be prevented.

Further, the cartridge 440 configured to accommodate the plurality of second tube connectors 106 and second tubes 102 is mountable to the attaching/detaching device 400 according to the fourth embodiment. With this, injection of the chemical liquid can be successively performed.

The present invention is described above referring to each of the embodiments. However, the present invention is not limited to the above-mentioned embodiments. The present invention also encompasses the invention modified within a scope not deviated from the present invention, and the invention equivalent to the present invention. Further, the each of the above-mentioned embodiments and each of the modifications may be combined with each other as appropriate within the scope not deviated from the present invention.

For example, a data carrier such as a radio frequency identifier (RFID) or a barcode can be provided to the syringe. Information of the chemical liquid having been charged is recorded on the data carrier. The multi-dose injection apparatus 608 is capable of reading out the recorded information from the data carrier and controlling an injection pressure of the chemical liquid.

Moreover, the multi-dose injection apparatus 608 can be connected to an imaging apparatus in a wire connection or in a wireless connection. At the time of injecting the chemical liquid and at the time of acquiring an image, the imaging apparatus and the multi-dose injection apparatus 608 communicate various pieces of data therebetween. In this case, for example, imaging acquisition protocols may be set or displayed on the multi-dose injection apparatus 608, or injection protocols may be set or displayed on the imaging apparatus. Examples of such imaging apparatus include various medical imaging apparatus such as a magnetic resonance imaging (MRI) apparatus, a computed tomography (CT) apparatus, an angiography imaging apparatus, a positron emission tomography (PET) apparatus, a single photon emission computed tomography (SPECT) apparatus, a CT angiography apparatus, an MR angiography apparatus, an ultrasonic diagnostic apparatus, and an angiographic imaging apparatus.

Moreover, the multi-dose injection apparatus 608 is also capable of transmitting information related to injection results (injection history) via a network to external storage devices such as a radiology information system (RIS), picture archiving and communication systems (PACS), and a hospital information system (HIS) and storing the information therein.

Moreover, the first tube connector 105 may be a connector configured to automatically close the flow passages at the time of non-connection. For example, the first tube connector 105 may be a connector of a type which achieves connection through insertion of the second tube connector 106 (male connector). Examples of the connector of this type include "SmartSite" manufactured by Becton Dickinson Japan and "Sureplug" (trademark) manufactured by Terumo Corporation. When the connector of this type is to be used, the holding portions for the second tube connector 106 hold the second tube connector 106 without rotating the second tube connector 106.

A part or all of the embodiments described above may be described also as given in the following remarks, but are not limited thereto.

(Remark 1)

A method of injecting a chemical liquid, comprising:

connecting a first tube to a contrast-medium line and a physiological-saline-solution line connected to a multi-dose injection apparatus including an attaching/detaching device, the attaching/detaching device including a fixing portion, a holding portion, and a moving portion;

fixing a first tube connector of the first tube with the fixing portion;

connecting a subject line to a second tube;

holding a second tube connector of the second tube with the holding portion;

connecting the second tube connector to the first tube connector by moving the holding portion, which holds the second tube connector, with the moving portion in a direction of approaching the first tube connector;

injecting a chemical liquid through the first tube and the second tube; and after injecting the chemical liquid, releasing the connection of the second tube connector and the first tube connector by moving the holding portion, which holds the second tube connector, with the moving portion in a direction of separating from the first tube connector.

(Remark 2)

The method of injecting a chemical liquid according to Remark 1, further comprising, after fixing the first tube connector with the fixing portion, closing a flow passage of the first tube with a closing member.

(Remark 3)

The method of injecting a chemical liquid according to Remark 1 or 2, further comprising, after holding the second tube connector with the holding portion, closing a flow passage of the second tube with a closing member.

(Remark 4)

The method of injecting a chemical liquid according to Remark 2 or 3, further comprising, after closing the flow passage, connecting the second tube connector to the first tube connector by moving the holding portion, which holds the second tube connector, with the moving portion in a direction of approaching the first tube connector.

This application claims the benefit of priority from Japanese Patent Application No. 2017-145844, filed on Jul. 27, 2017, the content of which is incorporated herein by reference.

REFERENCE SIGNS LIST

100: attaching/detaching device, 101a: first closing member, 101b: second closing member, 102: second tube, 103: first tube, 104: fixing portion, 105: first tube connector, 106: second tube connector, 107: holding portion, 108: moving portion, 200: attaching/detaching device, 204: fixing portion, 207b: holding portion, 208: moving portion, 221: removing member, 222a: first cap, 222b: second cap, 300: attaching/detaching device, 304: fixing portion, 308: moving portion, 321*a*: removing member, 321*b*: removing member, 400: attaching/detaching device, 404: fixing portion, 408: moving portion, 440: cartridge, 530: sensor, 608: multi-dose injection apparatus

The invention claimed is:

1. An attaching/detaching device comprising:
a fixing portion configured to fix a first tube connector;
holding portions configured to rotatably hold a second tube connector, the holding portions including a pair of the holding portions each having a roller shape; and
a moving portion configured to move the holding portions, which hold the second tube connector, in a first direction to connect the second tube connector to the first tube connector, and move the second tube connector after the connection in a second direction opposite to the first direction to release the connection of the second tube connector and the first tube connector, wherein
the second tube connector is nipped by the pair of the holding portions;
the second tube connector and the pair of the holding portions are disposed on the moving portion; and
the holding portions rotate the second tube connector together with a movement of the moving portion.

2. The attaching/detaching device according to claim 1, wherein the holding portions rotate in a forward direction while being moved in the first direction to threadingly engage the second tube connector to the first tube connector, and the holding portions rotate in a reverse direction while being moved in the second direction to release the threaded engagement of the second tube connector and the first tube connector.

3. The attaching/detaching device according to claim 1, further comprising a first closing member configured to close a first tube including the first tube connector.

4. The attaching/detaching device according to claim 3, wherein the first closing member is disposed on the moving member, and the first closing member is able to close the first tube when the second tube connector is connected to the first tube connector.

5. The attaching/detaching device according to claim 1, further comprising a second closing member configured to close a second tube including the second tube connector.

6. The attaching/detaching device according to claim 1, further comprising a sensor configured to detect air inside a first tube including the first tube connector or a second tube including the second tube connector, or a sensor configured to detect a flow of a chemical liquid inside the first tube or the second tube.

7. The attaching/detaching device according to claim 1, further comprising a removing member configured to remove a cap mounted to at least one of the first tube connector and the second tube connector.

8. The attaching/detaching device according to claim 7, wherein the removing member is configured to strike the cap.

9. The attaching/detaching device according to claim 7, wherein the removing member is configured to rotate the cap.

10. The attaching/detaching device according to claim 1, further comprising a cartridge configured to accommodate a plurality of second tube connectors.

11. The attaching/detaching device according to claim 1, wherein the moving portion and the fixing portion form a telescoping structure.

12. The attaching/detaching device according to claim 1, wherein the pair of holding portions are each connected to a drive shaft of the moving portion via a gear train, a belt, or a pulley.

13. A multi-dose injection apparatus comprising an attaching/detaching device comprising:
a fixing portion configured to fix a first tube connector;
holding portions configured to rotatably hold a second tube connector, the holding portions including a pair of the holding portions each having a roller shape; and
a moving portion configured to move the holding portion, which holds the second tube connector, in a first direction to connect the second tube connector to the first tube connector, and move the second tube connector after the connection in a second direction from opposite to the first direction to release the connection of the second tube connector and the first tube connector, wherein
the second tube connector is nipped by the pair of the holding portions;
the second tube connector and the pair of the holding portions are disposed on the moving portion;
the holding portions rotate the second tube connector together with a movement of the moving portion; and
the multi-dose injection apparatus is capable of performing multi-dose injection of a chemical liquid.

* * * * *